United States Patent
Han et al.

(10) Patent No.: US 11,136,478 B2
(45) Date of Patent: Oct. 5, 2021

(54) ACRYLIC ADHESIVE SHEET, MEDICAL ADHESIVE TAPE, AND METHOD FOR MANUFACTURING THE SAME

(71) Applicant: LG Chem, Ltd., Seoul (KR)

(72) Inventors: Jeong-In Han, Seoul (KR); Dan-A Kim, Seoul (KR); Jang-Soon Kim, Gyeonggi-do (KR); Seong-Hoon Yue, Gyeonggi-do (KR); Tae-Yi Choi, Gyeonggi-do (KR); Ji-Yeon Yang, Seoul (KR)

(73) Assignee: LG Chem, Ltd.

( * ) Notice: Subject to any disclaimer, the term of this patent is extended or adjusted under 35 U.S.C. 154(b) by 287 days.

(21) Appl. No.: 15/533,580

(22) PCT Filed: Dec. 22, 2015

(86) PCT No.: PCT/KR2015/014127
§ 371 (c)(1),
(2) Date: Jun. 6, 2017

(87) PCT Pub. No.: WO2016/105101
PCT Pub. Date: Jun. 30, 2016

(65) Prior Publication Data
US 2018/0010019 A1    Jan. 11, 2018

(30) Foreign Application Priority Data
Dec. 24, 2014    (KR) .................. 10-2014-0188050

(51) Int. Cl.
*C09J 7/38*      (2018.01)
*C09J 133/06*    (2006.01)
(Continued)

(52) U.S. Cl.
CPC ............... *C09J 7/385* (2018.01); *A61F 13/02* (2013.01); *A61F 13/0253* (2013.01); *C09J 4/00* (2013.01);
(Continued)

(58) Field of Classification Search
CPC ......... C09J 9/00; C09J 133/08; C09J 2203/30
See application file for complete search history.

(56) References Cited

U.S. PATENT DOCUMENTS 3,364,063 A * 1/1968 Donatas ................. A61L 15/58
264/41
3,908,650 A * 9/1975 Dunshee ................. A61L 15/26
428/315.9
(Continued)

FOREIGN PATENT DOCUMENTS

CA      1330503 C     7/1994
CN      1374848 A    10/2002
(Continued)

OTHER PUBLICATIONS

Search Report from State Intellectual Property Office in 1st Office Action for Chinese Application 201580070943.4 dated Jul. 27, 2018.
(Continued)

*Primary Examiner* — Chinessa T. Golden
(74) *Attorney, Agent, or Firm* — Lerner, David, Littenberg, Krumholz & Mentlik, LLP

(57) ABSTRACT

Provided are: an acrylic adhesive sheet having a porous structure including a plurality of pores and having a water vapor transmission rate of 2,000 g/m²·24 h to 3,500 g/m²·24 h at 24° C. and 25% RH, and a porosity of 10% to 60%; and a medical adhesive tape including the same.

16 Claims, 1 Drawing Sheet

(51) Int. Cl.
*C09J 7/10* (2018.01)
*C09J 4/00* (2006.01)
*A61F 13/02* (2006.01)
*C09J 9/00* (2006.01)
*C09J 133/08* (2006.01)
*C08K 5/25* (2006.01)
*C08K 3/26* (2006.01)
*C08K 5/23* (2006.01)

(52) U.S. Cl.
CPC . *C09J 7/10* (2018.01); *C09J 9/00* (2013.01); *C09J 133/06* (2013.01); *C09J 133/08* (2013.01); *C08K 5/23* (2013.01); *C08K 5/25* (2013.01); *C08K 2003/262* (2013.01); *C09J 2203/00* (2013.01); *C09J 2301/312* (2020.08); *C09J 2301/408* (2020.08); *C09J 2400/24* (2013.01); *C09J 2400/263* (2013.01); *C09J 2400/283* (2013.01); *C09J 2433/00* (2013.01); *C09J 2467/005* (2013.01)

(56) References Cited

U.S. PATENT DOCUMENTS

| | | | |
|---|---|---|---|
| 5,409,472 | A | 4/1995 | Rawlings et al. |
| 5,947,917 | A * | 9/1999 | Carte ............... A61L 15/58 |
| | | | 602/52 |
| 6,171,985 | B1 * | 1/2001 | Joseph ............. A61L 15/585 |
| | | | 428/316.6 |
| 6,383,630 | B1 | 5/2002 | Jauchen et al. |
| 2002/0061948 | A1 | 5/2002 | Murakami et al. |
| 2003/0064190 | A1 | 4/2003 | Carte et al. |
| 2004/0065232 | A1 * | 4/2004 | Lykke ............... A61L 15/585 |
| | | | 106/680 |
| 2005/0084521 | A1 | 4/2005 | Hamada et al. |
| 2006/0154546 | A1 * | 7/2006 | Murphy ............ A61F 13/023 |
| | | | 442/286 |
| 2006/0173088 | A1 | 8/2006 | Nozaki et al. |
| 2007/0087133 | A1 | 4/2007 | Cho et al. |
| 2015/0265742 | A1 | 9/2015 | Nakagawa et al. |

FOREIGN PATENT DOCUMENTS

| | | |
|---|---|---|
| CN | 1174719 C | 11/2004 |
| CN | 104922721 A | 9/2015 |
| EP | 0896993 A1 | 2/1999 |
| EP | 1184039 A2 | 3/2002 |
| JP | S63097677 A | 4/1988 |
| JP | H11116927 A | 4/1999 |
| JP | 2002065841 A | 3/2002 |
| JP | 2011121925 A | 6/2011 |
| JP | 5342702 B1 | 11/2013 |
| KR | 20050036779 A | 4/2005 |
| KR | 20070041238 A | 4/2007 |
| KR | 20090086012 A | 8/2009 |
| TW | 200504099 A | 2/2005 |
| WO | 2009099263 A1 | 8/2009 |

OTHER PUBLICATIONS

Search Report from Taiwan Intellectual Property Office in 1st Office Action for Taiwanese Application 104142864 dated Jul. 5, 2018.
Search Report from International Application No. PCT/KR2015/014127, dated May 4, 2016.

* cited by examiner

[Figure 1]
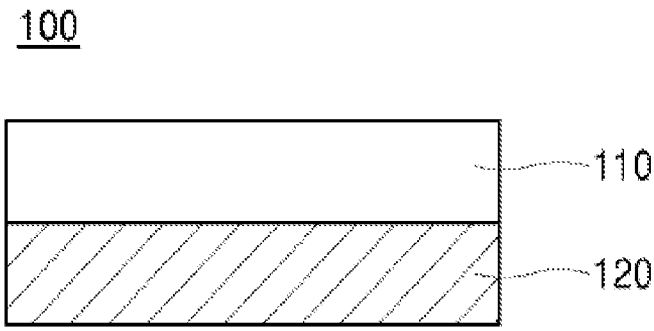
[Figure 2]
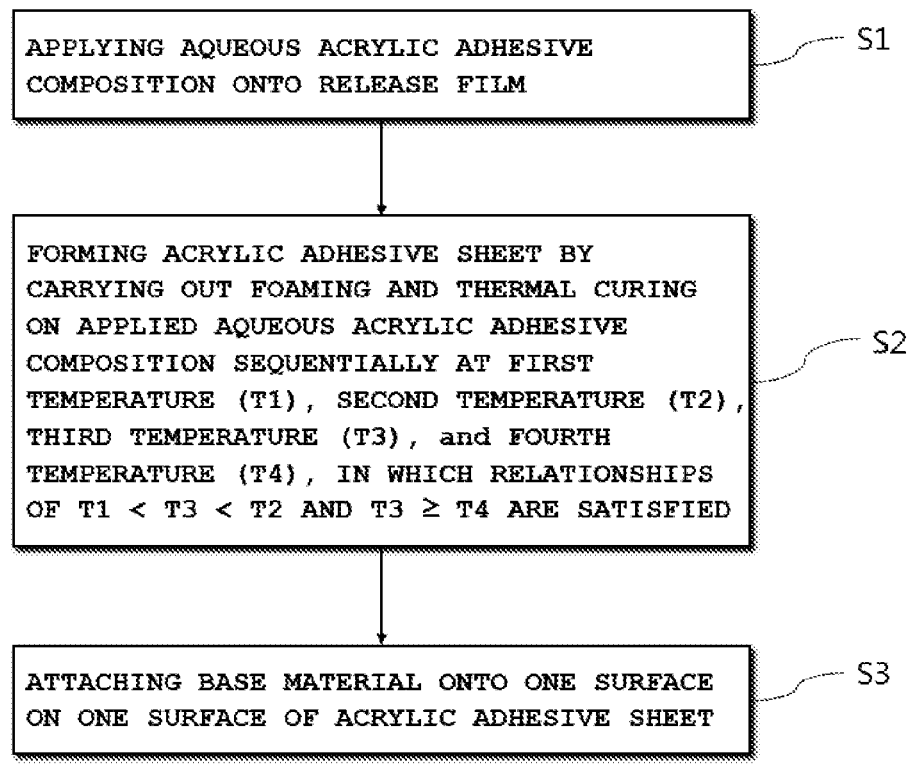

ACRYLIC ADHESIVE SHEET, MEDICAL ADHESIVE TAPE, AND METHOD FOR MANUFACTURING THE SAME

CROSS-REFERENCE TO RELATED APPLICATIONS

The present application is a national phase entry under 35 U.S.C. § 371 of International Application No. PCT/KR2015/014127 filed Dec. 22, 2015, which claims priority from Korean Application No. 10-2014-0188050 filed Dec. 24, 2014, all of which are incorporated herein by reference.

TECHNICAL FIELD

The present invention relates to an acrylic adhesive sheet, a medical adhesive tape, and a method for manufacturing the same.

BACKGROUND ART

An acrylic adhesive sheet is laminated on a base sheet and thus may be used as an acrylic adhesive tape, and the like, and the acrylic adhesive tape may be used for medical use in the medical field, and may be used as, for example, a surgical tape, a tape for surgical operation, an adhesive bandage, a first aid tape, a wound coating tape, a kinesiology tape, a sports tape, a sticking plaster, and the like.

The medical adhesive tape may serve to fix a medical device, a roller bandage, a wound protection dressing material, a wet dressing, a transdermal absorbent, and the like to the skin.

Typically, the adhesive tape may be formed by applying an adhesive onto a base sheet, and since the adhesive itself has a very low water vapor transmission property, moisture generated from the skin, and the like are not discharged when the adhesive tape is attached onto the skin for a long period of time, and accordingly, the stratum corneum of the skin is hydrated by moisture, and as a result, erosion or maceration, and the like may occur.

DETAILED DESCRIPTION OF THE INVENTION

Technical Problem

An exemplary embodiment of the present invention provides an acrylic adhesive sheet which simultaneously implements excellent air permeability, excellent water vapor transmission property, and excellent durability.

Another exemplary embodiment of the present invention provides a medical adhesive tape including the acrylic adhesive sheet.

Still another exemplary embodiment of the present invention provides a method for manufacturing the medical adhesive tape.

However, a technical problem to be achieved by the present invention is not limited to the aforementioned problem, and the other problems that are not mentioned may be clearly understood by the person skilled in the art from the following description.

Technical Solution

An exemplary embodiment of the present invention provides an acrylic adhesive sheet having a porous structure including a plurality of pores and having a water vapor transmission rate of about 2,000 g/m²·24 h to about 3,500 g/m²·24 h at about 24° C. and about 25% RH, and a porosity of about 10% to about 60%.

The pores may have an average size of about 500 nm to about 100 μm.

The acrylic adhesive sheet may have a thickness of about 10 μm to about 100 μm.

The acrylic adhesive sheet may be formed to have the porous structure by carrying out foaming and thermal curing on an aqueous acrylic adhesive composition.

The aqueous acrylic adhesive composition may include at least one selected from the group consisting of an acrylic resin, a surfactant, a thermal foaming agent, water, other additives, and a combination thereof.

The aqueous acrylic adhesive composition may or may not further include a separate cross-liking agent.

The aqueous acrylic adhesive composition may include the acrylic resin in an amount of about 40 wt % to about 70 wt %.

The aqueous acrylic adhesive composition may include a surfactant in an amount of about 1 wt % to about 10 wt %.

The surfactant may include at least one selected from the group consisting of a cationic surfactant, an anionic surfactant, an amphoteric surfactant, a non-ionic surfactant, and a combination thereof.

The acrylic resin may be formed by polymerizing a co-polymerizable monomer component including two or more acrylic monomers, and a content of acrylic acid in the total co-polymerizable monomers which form the acrylic resin may be about 0.7 wt % to about 2 wt %.

A content of methyl methacrylate in the total co-polymerizable monomers which form the acrylic resin may be more than about 0 wt % and about 10 wt %.

The aqueous acrylic adhesive composition may have a viscosity of about 1,000 cp to about 10,000 cp at about 25° C.

Another exemplary embodiment of the present invention provides a medical adhesive tape including the acrylic adhesive sheet.

Still another exemplary embodiment of the present invention provides a method for manufacturing a medical adhesive tape, the method including: applying an aqueous acrylic adhesive composition onto a release film; forming an acrylic adhesive sheet on the release film by carrying out foaming and thermal curing on the applied aqueous acrylic adhesive composition sequentially at a first temperature ($T_1$), a second temperature ($T_2$), a third temperature ($T_3$), and a fourth temperature ($T_4$); and attaching a base material onto one surface of the acrylic adhesive sheet, in which the first temperature to the fourth temperature satisfy the relationships of the first temperature ($T_1$)<the third temperature ($T_3$)<the second temperature ($T_2$) and the third temperature ($T_3$)≥the fourth temperature ($T_4$).

The first temperature may be formed at about 0° C. to about 80° C.

The second temperature may be formed at about 150° C. to about 200° C.

The third temperature may be formed at about 90° C. to about 120° C.

The fourth temperature may be formed at about 30° C. to about 120° C.

Foaming and thermal curing may be carried out at each of the first temperature, the second temperature, the third temperature, and the fourth temperature for about 0.5 minute to about 3 minutes.

The method may further include forming an aqueous acrylic adhesive composition by mixing at least two selected from the group consisting of an acrylic resin, a surfactant, a thermal foaming agent, water, other additives, and a combination thereof, in which a separate cross-linking agent may or may not be further mixed with the aqueous acrylic adhesive composition.

Advantageous Effects

The acrylic adhesive sheet and the medical adhesive tape may simultaneously implement excellent air permeability, excellent water vapor transmission property, and excellent durability.

BRIEF DESCRIPTION OF DRAWINGS

FIG. 1 is a schematic cross-sectional view of a medical adhesive tape according to another exemplary embodiment of the present invention.

FIG. 2 is a schematic process flow chart of a method for manufacturing a medical adhesive tape according to still another exemplary embodiment of the present invention.

BEST MODE

Hereinafter, exemplary embodiments of the present invention will be described in detail with reference to the accompanying drawings so that a person with ordinary skill in the art to which the present invention pertains can easily carry out the present invention. The present invention can be implemented in various different forms, and is not limited to the exemplary embodiments described herein.

To clearly describe the present invention, parts irrelevant to the description are omitted, and the same reference numerals will be given to the same or similar constituent elements throughout the specification.

In the drawings, the thicknesses of several layers and regions are enlarged so as to clearly express the layers and the regions. Moreover, in the drawings, the thicknesses of some layers and regions are exaggerated for convenience of explanation.

Hereinafter, the formation of any configuration at an upper portion (or a lower portion) of a base material or on (or below) of the base material means that any configuration is formed to be brought into contact with an upper surface (or a lower surface) of the base material, and does not exclude that another configuration is included between the base material and any configuration formed on (or below) the base material.

An exemplary embodiment of the present invention provides an acrylic adhesive sheet having a porous structure including a plurality of pores and having a water vapor transmission rate of, for example, about 2,000 g/m$^2$·24 h to about 3,500 g/mz$^2$·24 h at about 24° C. and about 25% RH, and a porosity of, for example, about 10% to about 60%. Specifically, the acrylic adhesive sheet may have a water vapor transmission rate of about 2,500 g/mz$^2$·24 h to about 3,500 g/mz$^2$·24 h at 24° C. and 25% RH, and a porosity of about 30% to about 60%.

A medical adhesive tape may be typically formed by applying an adhesive onto a base sheet, and since the adhesive itself has a significantly low water vapor transmission property, moisture generated from the skin, and the like are not discharged when the adhesive tape is attached onto the skin for a long period of time, and accordingly, the stratum corneum of the skin is hydrated by moisture, and as a result, erosion or maceration, and the like may occur.

Furthermore, since the erosion or maceration gradually weakens the strength of the stratum corneum of the skin, the stratum corneum is damaged when the adhesive tape is removed, and as a result, in a severe case, an external wound such as laceration of the skin is caused, and bacteria and the like may invade the damaged stratum corneum, thereby causing secondary damage such as occurrence of allergy or infection, and the like.

Thus, an exemplary embodiment has an advantage in that it is possible to simultaneously implement excellent air permeability, excellent water vapor transmission property, and excellent durability because the water vapor transmission rate of the acrylic adhesive sheet is formed at a sufficiently high level of, for example, about 2,000 g/m$^2$·24 h or more, and specifically, about 2,500 g/mz$^2$·24 h or more, and simultaneously, the porosity thereof is formed at an appropriate level of, for example, about 10% to 60%, and specifically, about 30% to about 60%.

Accordingly, when a medical adhesive tape including the acrylic adhesive sheet is attached onto the skin, the wearing sense is further improved, and moisture and the like discharged from the skin are easily discharged, and as a result, it is possible to prevent the above-described erosion or maceration of the skin, and the like and to effectively prevent secondary skin damage caused by the erosion or maceration, and the like.

Further, the medical adhesive tape uses an acrylic adhesive sheet and thus may implement excellent stability due to less irritation to the skin than the case of using a rubber-based adhesive sheet, and may implement excellent economic efficiency due to lower costs than the case of using a silicone-based adhesive sheet.

Typically, a porous structure includes a plurality of pores, the plurality of pores may be classified into two forms of, for example, a closed pore and an opened pore, and the porous structure may be formed to have a structure including each of the two forms or both the forms.

The closed pore may be referred to as a closed cell as a pore which is not connected to other pores because the pore is formed to have a structure in which the wall surfaces of the pore are all closed, and the opened pore may be referred to as an opened cell as a pore which is connected to other pores because the pore is formed to have a structure in which at least a portion of the wall surfaces of the pore is opened.

For example, the opened pore may be formed because during a process in which a foaming composition is foamed, gas generated from a foaming agent and the like in the foaming composition forms a bubble, and the bubble continues to be grown and then bursts, and specifically, the opened pore may be formed because as the bubble is growing, a bubble wall surface, which separates the bubble from adjacent bubbles, is gradually thinned, and as a result, the bubbles burst due to bursting or laceration of the bubble wall surface.

In an exemplary embodiment, the pores may have an average size of, for example, about 500 nm to about 100 μm, and specifically, 1 μm to 100 μm. The average size may mean an average diameter. Since the pores are formed to have an average size within the range, a wound site may be effectively protected by preventing various foreign substances and the like from invading the wound site from the outside while air or moisture may easily pass through the pores.

Further, the acrylic adhesive sheet may have a thickness of about 10 μm to about 100 μm. Since the acrylic adhesive sheet has a thickness within the range, a medical adhesive tape formed by including the acrylic adhesive sheet may implement excellent adhesive properties without excessively increasing the thickness thereof, and may sufficiently serve to protect a wound or an affected part.

Specifically, when the acrylic adhesive sheet has a thickness of less than about 10 μm, it may be difficult to form the acrylic adhesive sheet as a sheet having a porous structure, and when the acrylic adhesive sheet has a thickness of more than about 100 μm, it may be difficult to carry out a thermal curing reaction at a sufficiently uniform level as a whole. In an exemplary embodiment, the acrylic adhesive sheet may be formed to have the porous structure by carrying out foaming and thermal curing on an aqueous acrylic adhesive composition.

Specifically, during the process in which water is dried by thermally curing an acrylic resin having a large weight average molecular weight, and the like in an aqueous acrylic adhesive composition, the acrylic resins are entangled with each other to easily form a gel structure, and as a result, the gelation may be effectively conducted.

The aqueous acrylic adhesive composition may include at least one selected from the group consisting of an acrylic resin, a surfactant, a thermal foaming agent, water, other additives, and a combination thereof.

The acrylic resin may be formed by polymerizing a co-polymerizable monomer component including two or more acrylic monomers.

The co-polymerizable monomer component may include at least one selected from the group consisting of, for example, an alkyl group-containing (meth)acrylate, a hydroxyl group-containing (meth)acrylate, a carboxyl group-containing (meth)acrylate, and a combination thereof.

The co-polymerizable monomer component may include at least one selected from the group including, for example, methyl (meth)acrylate, ethyl (meth)acrylate, n-propyl (meth)acrylate, isopropyl (meth)acrylate, n-butyl (meth) acrylate, t-butyl (meth)acrylate, sec-butyl (meth) acrylate, pentyl (meth) acrylate, 2-ethylhexyl (meth) acrylate, 2-ethylbutyl (meth) acrylate, n-octyl (meth)acrylate, isooctyl (meth)acrylate, isononyl (meth)acrylate, lauryl (meth)acrylate, tetradecyl (meth)acrylate, acrylic acid, methacrylic acid, 2-hydroxyethyl (meth)acrylate, 2-hydroxypropyl (meth) acrylate, 4-hydroxybutyl (meth) acrylate, 6-hydroxyhexyl (meth)acrylate, 8-hydroxyoctyl (meth)acrylate, 2-hydroxyethylene glycol (meth)acrylate or 2-hydroxypropylene glycol (meth)acrylate, acrylic acid, and a combination thereof.

In an exemplary embodiment, the acrylic resin may be formed by polymerizing a co-polymerizable monomer component including acrylic acid.

A content of the acrylic acid in the total co-polymerizable monomers which form the acrylic resin may be, for example, about 0.7 wt % to about 2 wt %. Since the acrylic acid is included in a content within the range, the viscosity of the aqueous acrylic adhesive composition is appropriately adjusted, and as a result, excellent base material adhesion and excellent peel strength may be simultaneously implemented.

Further, the co-polymerizable monomer component may further include methyl methacrylate as a soft-type monomer.

A content of the methyl methacrylate in the total co-polymerizable monomers which form the acrylic resin may be, for example, more than about 0 wt % and about 10 wt %. Since the methyl methacrylate has a larger foaming space capable of generating a foam due to a structure in which a methyl group is bonded to alpha carbon, the foaming space may be sufficiently secured by including the methyl methacrylate in a content within the range, and as a result, the acrylic adhesive sheet may be easily formed to have a porous structure having a sufficiently high water vapor transmission property and an appropriate porosity.

The weight average molecular weight of the acrylic resin may be, for example, about 5,000,000 g/mol or more, and specifically, about 5,000,000 g/mol to about 10,000,000 g/mol, but is not limited thereto. Since the acrylic resin has a weight average molecular weight within the range, a gel structure may be sufficiently easily formed during a process in which water is dried without a cross-linking agent, and accordingly, the acrylic adhesive sheet may not include a cross-linking agent. Specifically, when the weight average molecular weight is less than about 5,000,000 g/mol, the gelation may be conducted at a required level only when a cross-linking agent is essentially included, and accordingly, cross-linking bonds are compactly formed so that it may be difficult for pores to be easily formed by gas.

The aqueous acrylic adhesive composition may include the acrylic resin in an amount of about 40 wt % to about 70 wt %. Since the aqueous acrylic adhesive composition includes the acrylic resin in a content within the range, the viscosity of the acrylic adhesive composition is adjusted at an appropriate level, and as a result, a porous structure of the acrylic adhesive sheet may be formed by foaming and thermal curing, such that the acrylic adhesive sheet has a sufficiently high-level water vapor transmission rate and an appropriate porosity to be implemented.

The aqueous acrylic adhesive composition may include water in an amount of about 20 wt % to about 50 wt %. Since the aqueous acrylic adhesive composition includes water in a content within the range, the viscosity of the aqueous acrylic adhesive composition may be appropriately adjusted.

The other additives may include at least one selected from the group consisting of, for example, a curing agent, a wetting agent, an antifoaming agent, a neutralizer, a thickener, a molecular weight adjusting agent, an emulsifier, a tackifier, an aqueous ammonia solution, and a combination thereof, but are not limited thereto.

The peel strength of the acrylic adhesive sheet may be appropriately adjusted by using, for example, a zinc oxide curing agent as the curing agent. In addition, the aqueous ammonia solution is used as a stabilizer of the aqueous acrylic adhesive composition, and may prevent a phenomenon in which physical properties of the aqueous acrylic adhesive composition are sharply changed when water is added in order to adjust the viscosity, and the like.

In an exemplary embodiment, the aqueous acrylic adhesive composition may include the surfactant, and may include the surfactant in an amount of about 1 wt % to about 10 wt %. Since the aqueous acrylic adhesive composition includes the surfactant in a content within the range, gas generated from a thermal foaming agent in the aqueous acrylic adhesive composition may be dissolved at an appropriate level during the foaming and thermal curing process, and accordingly, the acrylic adhesive sheet may be formed to have a porous structure having a sufficiently high water vapor transmission property and an appropriate porosity.

The surfactant may include at least one selected from the group consisting of, for example, a cationic surfactant, an anionic surfactant, an amphoteric surfactant, a non-ionic surfactant, and a combination thereof, and may include at least one selected from the group consisting of, for example, alkyl sulfate, alkyl aryl sulfate, alkyl aryl sulfonate, phosphate, alpha olefin sulfonate, ammonium laureth sulfate, ammonium laureth ether sulfate, ammonium stearate, sodium laureth sulfate, sodium octyl sulfate, sodium tridecyl ether sulfate, triethanolamine lauryl sulfate, disodium oleate, alkyl ether sulfate, sodium tri-oxyethylene lauryl ether sulfate (SLES), dimethyl lauryl amine oxide, and a combination thereof.

Furthermore, for example, the surfactant may include a silicone-based surfactant, a fluorine-based surfactant, or both the silicone-based surfactant and the fluorine-based surfactant, and accordingly, the surfactant may more easily dissolve bubbles in the acrylic adhesive composition, and may include at least one selected from the group consisting of, as a specific kind, a polyalkyleneoxidimethylsiloxane copolymer, an amino modified silicone-polyether copolymer, perfluorinated acid, perfluorinated sulfonate, and a combination thereof.

In an exemplary embodiment, the aqueous acrylic adhesive composition may include the thermal foaming agent in an amount of about 0.1 part by weight to about 5.0 parts by weight based on 100 parts by weight of the acrylic resin. Since the aqueous acrylic adhesive composition includes the thermal foaming agent in a content within the range, the acrylic adhesive sheet may simultaneously implement excellent water vapor transmission property and excellent durability by appropriately foaming the aqueous acrylic adhesive composition.

The thermal foaming agent may be, for example, an organic foaming agent, and may include at least one selected from the group consisting of, specifically, azo dicarbon amide, p,p'-oxybis(benzenesulfonyl hydrazide), p-toluenesulfonyl hydrazide, sodium bicarbonate, and a combination thereof. The organic foaming agent may be decomposed by carrying out a heat treatment at a high temperature of, for example, about 150° C. to about 180° C. for about 10 minutes or less, and accordingly, the organic foaming agent may cause foaming by releasing gas such as nitrogen while preventing an acrylic monomer, an acrylic resin, and the like from being damaged.

Meanwhile, an inorganic foaming agent may be decomposed only when a heat treatment is carried out at a high temperature of usually about 200° C. for about 10 minutes or less, and as a result, the inorganic foaming agent may damage an acrylic monomer, and acrylic resin, and the like.

The aqueous acrylic adhesive composition may or may not further include a separate cross-liking agent.

As described above, since an aqueous acrylic adhesive composition is used, a gelation may be easily conducted without a separate cross-linking agent, and accordingly, a plurality of pores may be easily formed by gas generated from a thermal foaming agent unlike a general cross-linking process caused by a cross-linking agent, so that a porous structure having excellent water vapor transmission property may be effectively formed.

Meanwhile, the aqueous acrylic adhesive composition may include a separate cross-linking agent according to the purpose and use of the invention, and the aqueous acrylic adhesive composition may decrease the peel strength of the acrylic adhesive sheet by including a separate cross-linking agent. As the cross-linking agent, those publicly known in the art may be used, and the cross-linking agent is not particularly limited.

Meanwhile, in the case of an oily acrylic adhesive composition, a separate cross-linking agent needs to be essentially added in order to conduct the gelation at a required level because resins having a small weight average molecular weight are used, and accordingly, there is a problem in that cross-linking bonds are compactly formed so that it is difficult to easily form pores by gas.

In an exemplary embodiment, at the time of initiating the foaming and thermal curing, the aqueous acrylic adhesive composition may have a viscosity of about 1,000 cp to about 10,000 cp at about 25° C. Since the aqueous acrylic adhesive composition has a viscosity within the range, the water vapor transmission rate and porosity of an acrylic adhesive sheet having a porous structure formed by carrying out foaming and thermal curing on the aqueous acrylic adhesive composition are appropriately coordinated, and as a result, excellent water vapor transmission property and excellent durability may be simultaneously implemented.

The acrylic adhesive sheet implements excellent air permeability, excellent water vapor transmission property, and excellent durability as described above, and accordingly, when the acrylic adhesive sheet is attached onto the skin, the wearing sense is further improved, and moisture and the like discharged from the skin are easily discharged, and as a result, it is possible to prevent the above-described erosion or maceration of the skin, and the like and to effectively prevent secondary skin damage caused by the erosion or maceration, and the like, and as a result, the acrylic adhesive sheet may be applied specifically for a medical adhesive tape use.

Another exemplary embodiment of the present invention provides a medical adhesive tape including the acrylic adhesive sheet. The acrylic adhesive sheet is the same as that described in an exemplary embodiment.

FIG. 2 schematically illustrates a cross sectional view of a medical adhesive tape 100. The medical adhesive tape 100 includes a base material 120 and an acrylic adhesive sheet 110 laminated on one surface of the base material 120.

As described above, there is an advantage in that it is possible to simultaneously implement excellent water vapor transmission property, and excellent durability because the water vapor transmission rate of the acrylic adhesive sheet 110 is formed at a sufficiently high level of, for example, about 2,000 g/m$^2$·24 h or more, and specifically, about 2,500 g/m$^2$·24 h or more and simultaneously, the porosity thereof is formed at an appropriate level of, for example, about 10% to 60%, and specifically, about 30% to about 60%.

Accordingly, when the medical adhesive tape 100 including the acrylic adhesive sheet 110 is attached onto the skin, the wearing sense is further improved and moisture and the like discharged from the skin are easily discharged, and as a result, it is possible to prevent the above-described erosion or maceration of the skin, and the like and to effectively prevent secondary skin damage caused by the erosion or maceration, and the like.

The base material 120 may be formed of a material including at least one selected from the group consisting of a fabric or non-woven fabric of an organic fiber or inorganic fiber material, paper, and a combination thereof, but is not limited thereto.

The base material 120 may have a thickness of, for example, about 50 μm to about 200 μm, but the thickness is not limited thereto. Since the base material 120 has a thickness within the range, the base material 120 may sufficiently support the acrylic adhesive sheet 110 without extremely increasing the thickness of the medical adhesive tape 100.

Further, the acrylic adhesive sheet 110 may have a thickness of about 10 μm to about 100 μm. Since the acrylic adhesive sheet 110 has a thickness within the range, the medical adhesive tape 100 may implement excellent adhesive property without excessively increasing the thickness thereof, and may sufficiently serve to protect an affected part.

Still another exemplary embodiment of the present invention provides a method for manufacturing a medical adhesive tape, and FIG. 2 schematically illustrates a process flow chart of the manufacturing method.

The manufacturing method includes: applying an aqueous acrylic adhesive composition onto a release film (S1); forming an acrylic adhesive sheet on the release film by carrying out foaming and thermal curing on the applied aqueous acrylic adhesive composition sequentially at a first temperature ($T_1$), a second temperature ($T_2$), a third temperature ($T_3$), and a fourth temperature ($T_4$) (S2); and attaching a base material onto one surface of the acrylic adhesive sheet (S3), in which the first temperature to the fourth temperature satisfy the relationships of the first temperature ($T_1$)<the third temperature ($T_3$)<the second temperature ($T_2$) and the third temperature ($T_3$)≥the fourth temperature ($T_4$).

By the manufacturing method, the acrylic adhesive sheet described in an exemplary embodiment and the medical adhesive tape described in another exemplary embodiment may be manufactured.

As described above, the manufacturing method has an advantage in that it is possible to sufficiently carry out foaming and thermal curing reactions while effectively preventing the acrylic resin from being damaged because in an acrylic adhesive sheet included in a medical adhesive tape manufactured by the manufacturing method, the time for applying a high-temperature process is appropriately decreased by appropriately adjusting the temperature conditions at each predetermined time interval while carrying out the foaming and thermal curing.

As a result, it is possible to simultaneously implement excellent water vapor transmission property, and excellent durability because the water vapor transmission rate of the acrylic adhesive sheet manufactured by the method is formed at a sufficiently high level of, for example, about 2,000 g/m²·24 h or more, and specifically, about 2,500 g/m²·24 h or more, and simultaneously, the porosity thereof is formed at an appropriate level of, for example, about 10% to 60%, and specifically, about 30% to about 60%.

Accordingly, when a medical adhesive tape including the acrylic adhesive sheet is attached onto the skin, the wearing sense is further improved, and moisture and the like discharged from the skin are easily discharged, and as a result, it is possible to prevent the above-described erosion or maceration of the skin, and the like and to effectively prevent secondary skin damage caused by the erosion or maceration, and the like.

The aqueous acrylic adhesive composition and the base material are the same as those described above in an exemplary embodiment.

In the manufacturing method, an aqueous acrylic adhesive composition may be applied onto a release film. The release film may be, for example, a thermoplastic plastic film, and may be, for example, a polyethylene terephthalate (PET) film, but is not limited thereto.

Subsequently, in the manufacturing method, an acrylic adhesive sheet may be formed on the release film by carrying out foaming and thermal curing on the applied aqueous acrylic adhesive composition sequentially at a first temperature ($T_1$), a second temperature ($T_2$), a third temperature ($T_3$), and a fourth temperature ($T_4$), and the first temperature to the fourth temperature satisfy the relationships of the first temperature ($T_1$)<the third temperature ($T_3$)<the second temperature ($T_2$) and the third temperature ($T_3$) the fourth temperature ($T_4$).

That is, while foaming and thermal curing are carried out on the applied aqueous acrylic adhesive composition, the foaming and thermal curing may be continuously carried out at the first temperature ($T_1$), the second temperature ($T_2$), the third temperature ($T_3$), and the fourth temperature ($T_4$) by changing the temperature within each temperature range to be described below two times or three times.

Specifically, the first temperature may be formed at about 0° C. to about 80° C. Since the first temperature is formed within the temperature range, the thermal curing reaction may be appropriately carried out while evaporating a solvent included in the applied aqueous acrylic adhesive composition.

Further, the second temperature may be formed at about 150° C. to about 200° C. Since the thermal foaming agent may be sufficiently decomposed by setting the second temperature within the temperature range, the foaming and thermal curing may be effectively carried out.

In addition, the third temperature may be formed at about 90° C. to about 120° C. After the thermal foaming agent is sufficiently decomposed by the second temperature, the temperature may be lowered to the temperature range to smoothly carry out the foaming and thermal curing reactions while effectively preventing the acrylic resin from being damaged.

Furthermore, the fourth temperature may be formed at about 30° C. to about 120° C., and within the range, the forth temperature may be equal to or lower than the third temperature because the fourth temperature satisfies the relationship of the third temperature ($T_3$)≥the fourth temperature ($T_4$) as described above. By setting the fourth temperature within the temperature range, it is possible to effectively prevent the acrylic resin from being damaged while sufficiently carrying out the foaming and thermal curing reactions.

In the manufacturing method, foaming and thermal curing may be carried out at each of the first temperature, the second temperature, the third temperature, and the fourth temperature for about 0.5 minute to about 3 minutes. By appropriately adjusting each time when the foaming and thermal curing are carried out at each temperature, the thermal foaming agent is sufficiently decomposed to easily initiate the foaming, and the acrylic resin, and the like are effectively prevented from being damaged, and as a result, the acrylic adhesive sheet may be formed to have a porous structure having excellent water vapor transmission property and an appropriate porosity.

In the manufacturing method, a base material may be attached onto one surface of the acrylic adhesive sheet, may be attached by a method publicly known in the art, and may be attached by, for example, a publicly known lamination process, but the attachment method is not limited thereto.

The medical adhesive tape may be distributed and sold, for example, while the release film is attached, or may be distributed and sold in a roll form in which the medical adhesive tape is wound while the release film is removed.

In addition, the manufacturing method may further include forming an aqueous acrylic adhesive composition by mixing at least two selected from the group consisting of an acrylic resin, a surfactant, a thermal foaming agent, water, other additives, and a combination thereof.

Furthermore, a separate cross-linking agent may or may not be further mixed with the aqueous acrylic adhesive composition, and the cross-linking agent is the same as that described above in an exemplary embodiment.

Hereinafter, specific examples of the present invention will be suggested. However, the Examples described below are only provided for specifically exemplifying or explaining the present invention, and the present invention is not limited thereby.

EXAMPLES

Example 1

An acrylic resin having a weight average molecular weight of 10,000,000 g/mol was formed by polymerizing a co-polymerizable monomer component including 0.7 wt % of acrylic acid (AA), 3 wt % of methyl methacrylate (MMA), 13 wt % of ethylhexyl acrylate (EHA), 12 wt % of ethyl acrylate (EA), and 30 wt % of butyl acrylate (BA).

Subsequently, an aqueous acrylic adhesive composition was formed by mixing and stirring 54.2 wt % of the acrylic resin, 0.9 part by weight of p,p'-oxybis(benzenesulfonyl hydrazide) as a thermal foaming agent, 41.5 wt % of water, 1.3 wt % of poly(ethyleneglycol)nonylphenyletherammoniumsulfate (emulsifier), and 1.2 wt % of N,N-dimethyl lauryl amine oxide, and the aqueous acrylic adhesive composition had a viscosity of 8,748 cp at 25° C. A content of the thermal foaming agent was based on 100 parts by weight of the acrylic resin.

Subsequently, the aqueous acrylic adhesive composition was applied to have a thickness of 130 μm onto a release film formed of a PET material having a thickness of 75 μm, and an acrylic adhesive sheet having a thickness of 70 μm was manufactured on the release film by carrying out foaming and thermal curing on the applied aqueous acrylic adhesive composition sequentially at a first temperature ($T_1$), a second temperature ($T_2$), a third temperature ($T_3$), and a fourth temperature ($T_4$).

The first temperature was 80° C., the second temperature was 156° C., the third temperature was 100° C., and the fourth temperature was 60° C., and the foaming and thermal curing were carried out at each of the temperatures for 3 minutes.

Further, subsequently, a medical adhesive tape was manufactured by attaching a base material formed of a paper material onto one surface of the acrylic adhesive sheet.

Comparative Example 1

Carrying Out Foaming and Thermal Curing at High Temperature)

An aqueous acrylic adhesive composition was prepared according to the same condition and method as those in Example 1.

Subsequently, the aqueous acrylic adhesive composition was applied to have a thickness of 130 μm onto a release film formed of a PET material having a thickness of 75 μm, foaming and thermal curing were carried out, and an acrylic adhesive sheet having a thickness of 75 μm was manufactured on the release film by carrying out the foaming and thermal curing at 180° C. for 6 minutes by maintaining a predetermined temperature while carrying out the foaming and thermal curing.

Further, subsequently, a medical adhesive tape was manufactured by attaching a base material formed of a paper material onto one surface of the acrylic adhesive sheet.

Comparative Example 2

Carrying Out Foaming and Thermal Curing at Low Temperature

An aqueous acrylic adhesive composition was prepared according to the same condition and method as those in Example 1.

Subsequently, the aqueous acrylic adhesive composition was applied to have a thickness of 130 μm onto a release film formed of a PET material having a thickness of 75 μm, foaming and thermal curing were carried out, and an acrylic adhesive sheet having a thickness of 75 μm was manufactured on the release film by lowering the temperature one time and carrying out the foaming and thermal curing sequentially at a first temperature and a second temperature while carrying out the foaming and thermal curing.

The temperature was 120° C. and the second temperature was 180° C., and the foaming and thermal curing were carried out at each temperature for 6 minutes.

Further, subsequently, a medical adhesive tape was manufactured by attaching a base material formed of a paper material onto one surface of the acrylic adhesive sheet.

Experimental Examples

Physical properties of the acrylic adhesive sheets included in the medical adhesive tapes according to Example 1 and Comparative Examples 1 and 2 were evaluated, and are shown in the following Table 1.

Evaluation Method (Water Vapor Transmission Rate)

Measurement method: measured by a water method in accordance with the ASTM E 96 conditions.

Specifically, a circle-shaped sample having a diameter of 46 mm was prepared by cutting each acrylic adhesive sheet, an initial weight being a weight before each sample was put into a constant temperature and constant humidity chamber was measured, a post weight being a weight after each sample was left to stand at 40° C. and 20 RH % in the constant temperature and constant humidity chamber for 24 hours was measured, and then a water vapor transmission rate was calculated by the following Equation 2.

$$\text{Water vapor transmission rate } (g/m^2 \cdot 24\ h) = (\text{initial weight} - \text{post weight})/\text{area} \quad \text{[Equation 2]}$$

(Density)

Measurement method: A sample with a size of 5 cm×5 cm×50 μm was prepared by cutting each acrylic adhesive sheet, a volume of the sample was calculated, a mass thereof was measured, and then each density was calculated by dividing the mass by the volume.

(Porosity)

Measurement method: A density (d2) of a foamed acrylic adhesive sheet was calculated by measuring the mass and volume of each acrylic adhesive sheet by a method which is the same as the above-described density measurement method.

Further, a non-foamed acrylic adhesive sheet was manufactured by photo-curing an acrylic adhesive composition including the same components as those in Example 1, except that a nitrogen gas was not injected thereinto. In addition, a non-foamed acrylic adhesive sheet was manufactured by photo-curing an acrylic adhesive composition including the same components as those in Comparative Example 1, except that the foaming agent was not mixed, and a non-foamed acrylic adhesive sheet was manufactured by thermally curing an acrylic adhesive composition including the same components as those in Comparative Example 2, except that the foaming agent was not mixed.

A density (d1) of a non-foamed acrylic adhesive sheet was calculated by measuring the mass and volume of each non-foamed acrylic adhesive sheet by a method which is the same as the above-described density measurement method.

A porosity was calculated by putting the density (d2) of the foamed acrylic adhesive sheet and the density (d1) of the non-foamed acrylic adhesive sheet, which were calculated as described above, into the following Equation 1.

$$\text{Porosity (\%)} = (d_1 - d_2)/d_2 \times 100 \quad \text{[Equation 1]}$$

TABLE 1

|  | Density (g/cm³) | Water vapor transmission rate (g/m² · 24 h) | Porosity (%) |
| --- | --- | --- | --- |
| Example 1 | 0.705 | 2818 | 42 |
| Comparative Example 1 | 0.873 | 1354 | 15 |
| Comparative Example 2 | 0.844 | 863 | 18 |

In the acrylic adhesive sheet according to Example 1, the density and the porosity were formed at an appropriate level of 0.705 g/cm³ and 42%, respectively, and the water vapor transmission rate was formed at a sufficiently high level of 2,818 g/m²·24 h, and as a result, the acrylic adhesive sheet according to Example 1 could simultaneously implement excellent water vapor transmission rate and excellent durability.

In contrast, the acrylic adhesive sheets according to Comparative Examples 1 and 2 had excellent durability due to the density of more than 0.87 g/cm³ and the porosity of less than 18.0%, but had the water vapor transmission rate of less than 1,400 g/m²·24 h, which was significantly low, and as a result, when medical adhesive tapes including the acrylic adhesive sheets according to Comparative Examples 1 and 2 are attached onto the skin for a long period of time, it is possible to clearly expect that moisture generated from the skin, and the like are not discharged, and accordingly, the stratum corneum of the skin is hydrated by moisture, and as a result, erosion or maceration, and the like occur.

EXPLANATION OF REFERENCE NUMERALS AND SYMBOLS

100: Medical adhesive tape
110: Acrylic adhesive sheet
120: Base material

The invention claimed is:

1. An acrylic adhesive sheet having a porous structure comprising a plurality of pores and having a water vapor transmission rate of 2,000 g/m²·24 h to 3,500 g/m²·24 h at 24° C. and 25% RH, and a porosity of 30% to 60%,
    wherein the water vapor transmission rate is measured in accordance with ASTM E 96 conditions,
    wherein the acrylic adhesive sheet is formed to have the porous structure by carrying out foaming and thermal curing on an aqueous acrylic adhesive composition sequentially at a first temperature (T1), a second temperature (T2), a third temperature (T3), and a fourth temperature (T4),
    wherein the aqueous acrylic adhesive composition comprises at least one selected from the group consisting of an acrylic resin, a surfactant, a thermal foaming agent, water, and other additives, wherein the other additives are at least one selected from the group consisting of a curing agent, a wetting agent, an antifoaming agent, a neutralizer, a thickener, a molecular weight adjusting agent, an emulsifier, a tackifier, and an aqueous ammonia solution,
    wherein the acrylic resin is formed by polymerizing a co-polymerizable monomer component comprising two or more acrylic monomers, and a content of acrylic acid in the total co-polymerizable monomers which form the acrylic resin is 0.7 wt % to 2 wt %, and a content of methyl methacrylate in the total co-polymerizable monomers which form the acrylic resin is more than 0 wt % and 10 wt %.

2. The acrylic adhesive sheet of claim 1, wherein the pores have an average size of 500 nm to 100 μm.

3. The acrylic adhesive sheet of claim 1, wherein the acrylic adhesive sheet has a thickness of 10 μm to 100 μm.

4. The acrylic adhesive sheet of claim 1, wherein the aqueous acrylic adhesive composition comprises the acrylic resin in an amount of 40 wt % to 70 wt %.

5. The acrylic adhesive sheet of claim 1, wherein the aqueous acrylic adhesive composition comprises a surfactant in an amount of 1 wt % to 10 wt %.

6. The acrylic adhesive sheet of claim 5, wherein the surfactant comprises at least one selected from the group consisting of a cationic surfactant, an anionic surfactant, an amphoteric surfactant, a non-ionic surfactant, and a combination thereof.

7. The acrylic adhesive sheet of claim 1, wherein the aqueous acrylic adhesive composition has a viscosity of 1,000 cp to 10,000 cp at 25° C.

8. The acrylic adhesive sheet of claim 1, wherein the aqueous acrylic adhesive composition further comprises or does not further comprise a separate cross-liking agent.

9. A medical adhesive tape comprising the acrylic adhesive sheet according to claim 1.

10. A method for manufacturing a medical adhesive tape of claim 9, the method comprising:
    applying an aqueous acrylic adhesive composition onto a release film;
    forming an acrylic adhesive sheet on the release film by carrying out foaming and thermal curing on the applied aqueous acrylic adhesive composition sequentially at a first temperature ($T_1$), a second temperature ($T_2$), a third temperature ($T_3$), and a fourth temperature ($T_4$); and
    attaching a base material onto one surface of the acrylic adhesive sheet,
    wherein the first temperature to the fourth temperature satisfy the relationships of the first temperature ($T_1$) <the third temperature ($T_3$)<the second temperature ($T_2$) and the third temperature ($T_3$) >the fourth temperature ($T_4$).

11. The method of claim 10, wherein the first temperature is formed at 0° C. to 80° C.

12. The method of claim 10, wherein the second temperature is formed at 150° C. to 200° C.

13. The method of claim 10, wherein the third temperature is formed at 90° C. to 120° C.

14. The method of claim 10, wherein the fourth temperature is formed at 30° C. to 120° C.

15. The method of claim 10, wherein foaming and thermal curing are carried out at each of the first temperature, the second temperature, the third temperature, and the fourth temperature for 0.5 minute to 3 minutes.

16. The method of claim 10, further comprising:
    forming an aqueous acrylic adhesive composition by mixing at least two selected from the group consisting of an acrylic resin, a surfactant, a thermal foaming agent, water, other additives, and a combination thereof, wherein a separate cross-linking agent is or is not further mixed with the aqueous acrylic adhesive composition.

* * * * *